(12) United States Patent
von Lehe et al.

(10) Patent No.: US 9,220,873 B2
(45) Date of Patent: Dec. 29, 2015

(54) DOUBLE ENDED INTRAVASCULAR MEDICAL DEVICE

(71) Applicant: Covidien LP, Mansfield, MA (US)

(72) Inventors: Cathleen von Lehe, Rogers, MN (US); Richard S. Kusleika, Eden Prarie, MN (US); Brooke Ren, Maple Grove, MN (US); Thomas L. Clubb, Hudson, WI (US)

(73) Assignee: Covidien LP, Mansfield, MA (US)

( * ) Notice: Subject to any disclaimer, the term of this patent is extended or adjusted under 35 U.S.C. 154(b) by 212 days.

(21) Appl. No.: 13/746,429

(22) Filed: Jan. 22, 2013

(65) Prior Publication Data

US 2014/0039541 A1    Feb. 6, 2014

Related U.S. Application Data

(63) Continuation of application No. 12/620,212, filed on Nov. 17, 2009, now Pat. No. 8,435,256, which is a continuation of application No. 10/810,445, filed on Mar. 26, 2004, now Pat. No. 7,637,920.

(60) Provisional application No. 60/508,437, filed on Oct. 3, 2003, provisional application No. 60/458,884, filed on Mar. 28, 2003.

(51) Int. Cl.
*A61B 17/22* (2006.01)
*A61M 25/09* (2006.01)
(Continued)

(52) U.S. Cl.
CPC .............. *A61M 25/09* (2013.01); *A61F 2/013* (2013.01); *A61F 2002/011* (2013.01); *A61F 2002/018* (2013.01); *A61F 2230/008* (2013.01); *A61F 2230/0008* (2013.01); *A61M 25/00* (2013.01)

(58) Field of Classification Search
CPC . A61M 29/00; A61M 25/09; A61F 2002/011; A61F 2/013; A61F 2002/018; A61B 17/22
USPC .......................... 606/159, 108, 200; 604/528
See application file for complete search history.

(56) References Cited

U.S. PATENT DOCUMENTS

| 4,991,602 A | 2/1991 | Amplatz et al. |
| 5,059,183 A | 10/1991 | Semrad |

(Continued)

FOREIGN PATENT DOCUMENTS

| EP | 0 364 777 A1 | 4/1990 |
| EP | 0 365 269 A1 | 4/1990 |

(Continued)

OTHER PUBLICATIONS

Chester, "Permanent Transrectal Drainage of a Diverticular-Related Abscess With a Double-Ended Pigtail Catheter," Br J Surg, 75(6):562 (Jun. 1988).

(Continued)

*Primary Examiner* — Victor Nguyen

(57) ABSTRACT

An intravascular medical device including an elongated member configured to be advanced along a vascular path of a patient, the elongated member having opposite first and second ends, the first end and second ends both being adapted for intravascular insertion, and the first end having a different structure than the second end. The elongated member has sufficient flexibility to be advanced through a human vasculature. Preferably, the first and second ends are adapted to have different operating characteristics. Depending on the operating characteristics needed for a particular procedure, a physician can insert either the first end portion or the second end portion of the elongated member into the patient's vasculature.

32 Claims, 17 Drawing Sheets

(51) Int. Cl.
*A61F 2/01* (2006.01)
*A61M 25/00* (2006.01)

(56) References Cited

U.S. PATENT DOCUMENTS

| | | | |
|---|---|---|---|
| 5,069,225 | A | 12/1991 | Okamura |
| 5,112,327 | A | 5/1992 | Iinuma et al. |
| 5,176,626 | A | 1/1993 | Soehendra |
| 5,217,025 | A | 6/1993 | Okamura |
| 5,363,847 | A | 11/1994 | Viera |
| 5,498,240 | A | 3/1996 | Bagaoisan et al. |
| 5,662,703 | A * | 9/1997 | Yurek et al. .................. 623/1.12 |
| RE35,849 | E | 7/1998 | Soehendra |
| 5,925,059 | A | 7/1999 | Palermo et al. |
| 6,045,547 | A | 4/2000 | Ren et al. |
| 6,096,022 | A | 8/2000 | Laymon et al. |
| 6,152,946 | A | 11/2000 | Broome et al. |
| 6,361,546 | B1 | 3/2002 | Khosravi |
| 6,485,501 | B1 * | 11/2002 | Green ........................... 606/200 |
| 6,595,960 | B2 | 7/2003 | West et al. |
| 6,979,343 | B2 | 12/2005 | Russo et al. |
| 7,637,920 | B2 | 12/2009 | von Lehe et al. |
| 2002/0111649 | A1 | 8/2002 | Russo et al. |

FOREIGN PATENT DOCUMENTS

| | | |
|---|---|---|
| EP | 0 516 198 A1 | 12/1992 |
| EP | 0 761 250 A1 | 3/1997 |
| WO | WO96/01591 | 1/1996 |
| WO | WO01/70097 A1 | 9/2001 |

OTHER PUBLICATIONS

Cox, "Percutaneous Cystogastrostomy for Treatment of Pancreatic Pseudocysts," Aust N Z J Surg, 63(9):693-698 (Sep. 1993).
Feb. 28, 2005 Notification of Transmittal of the International Search Report and the Written Opinion of the International Searching Authority, or the Declaration in PCT/US2004/009518 (15 pages).
Sep. 29, 2004 Invitation to Pay Additional Fees and Partial International Search Report in PCT/US2004/009518 (5 pages).

* cited by examiner

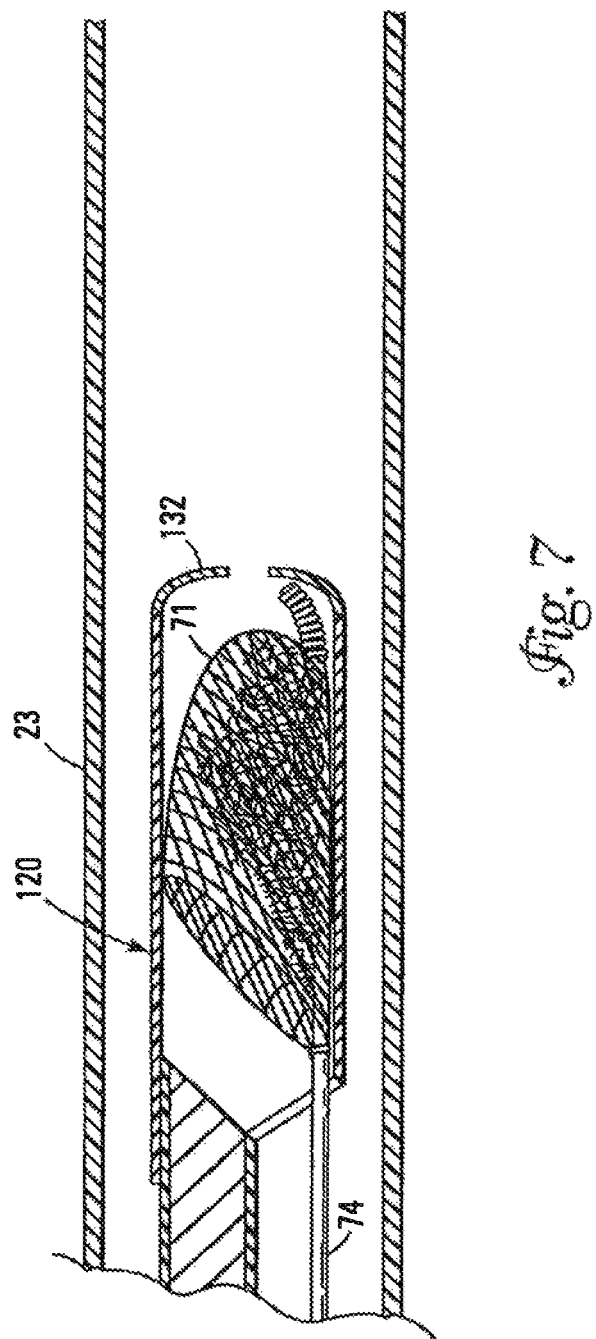

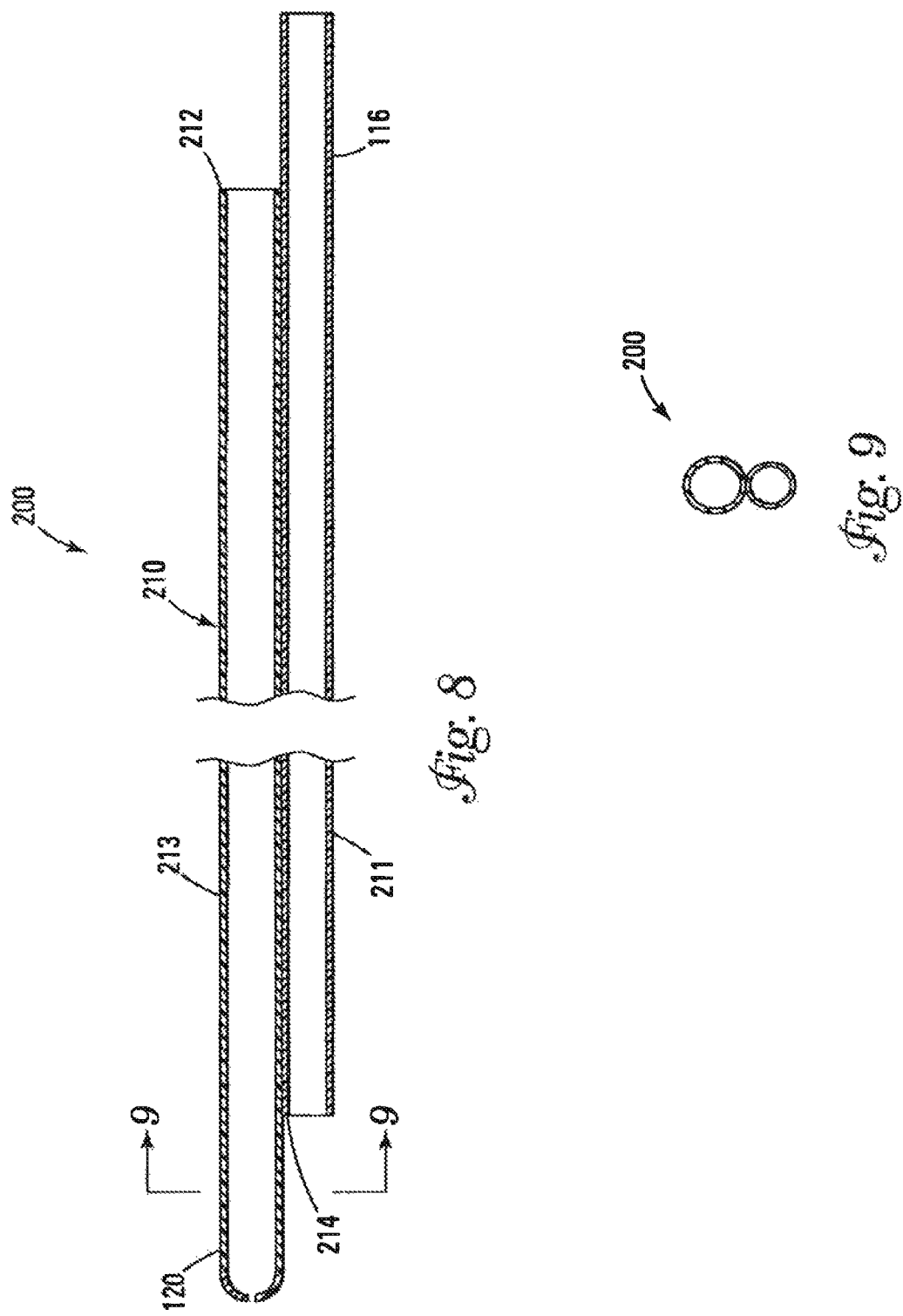

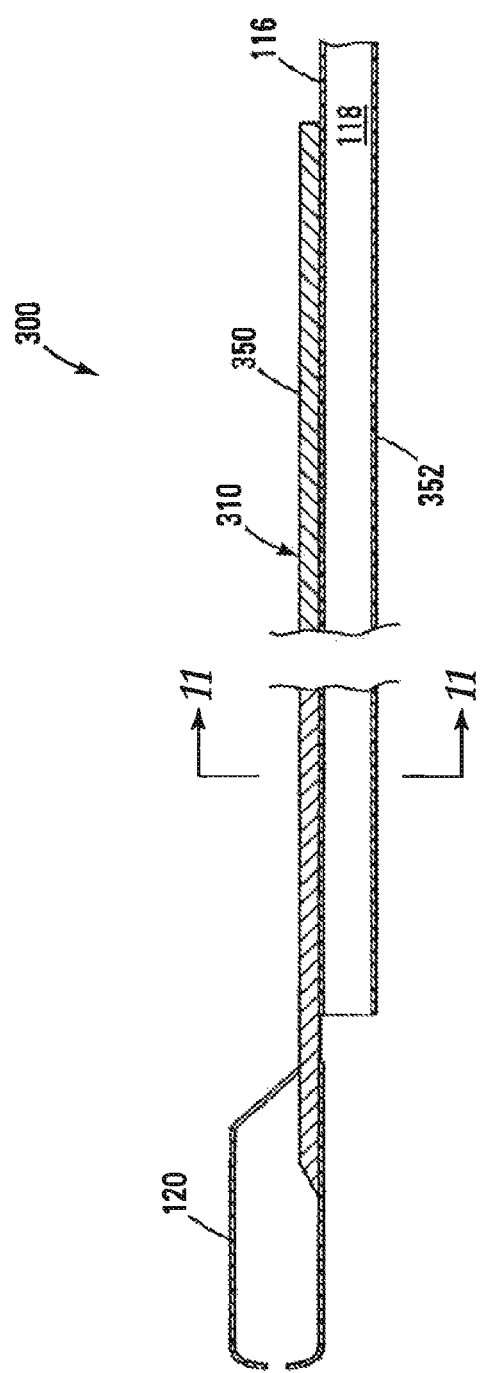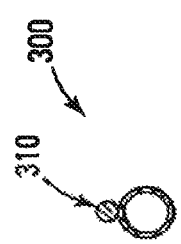

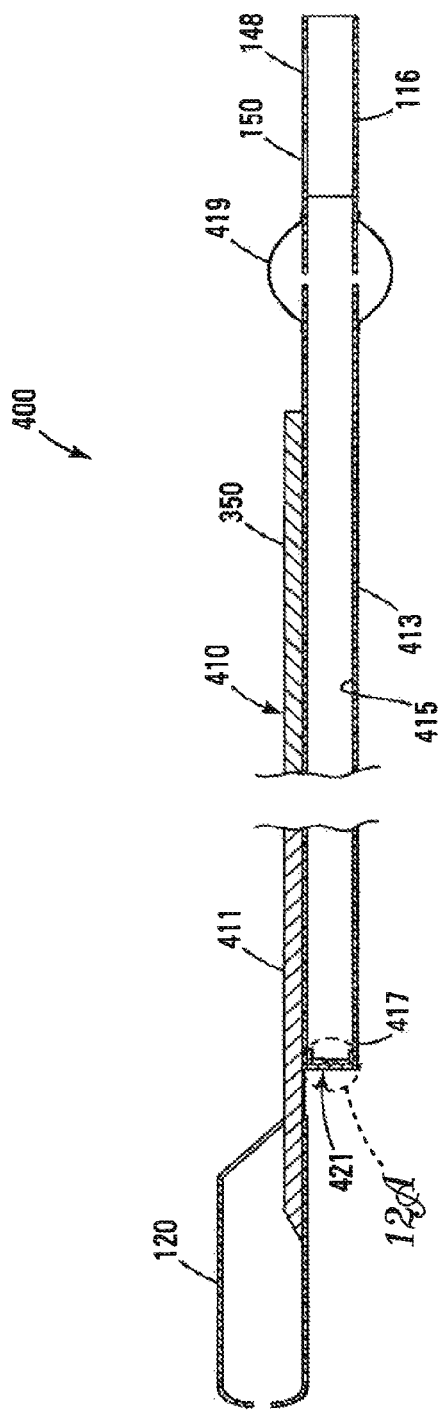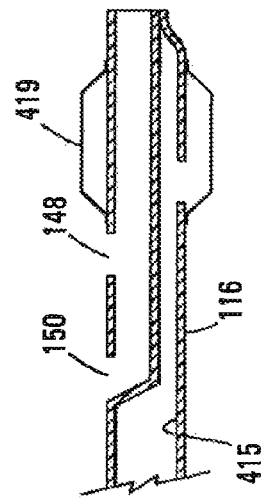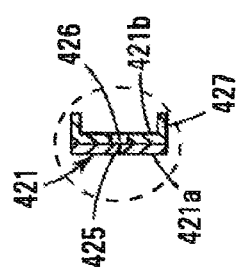

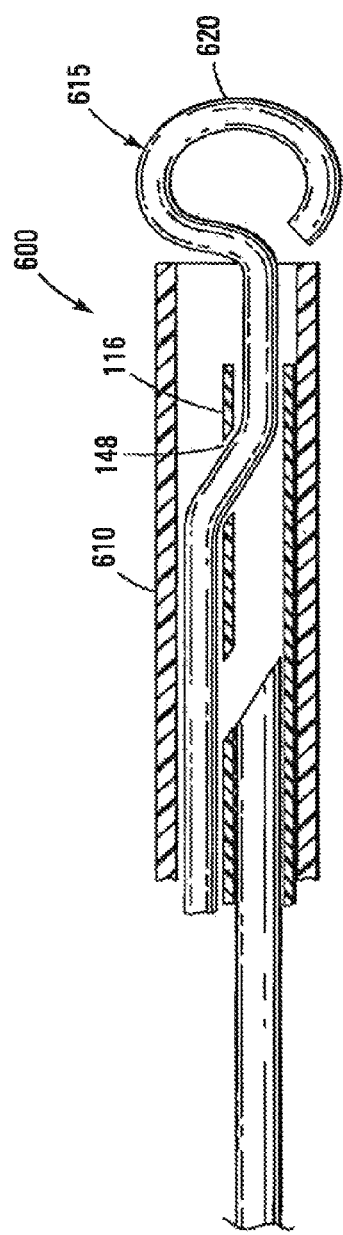
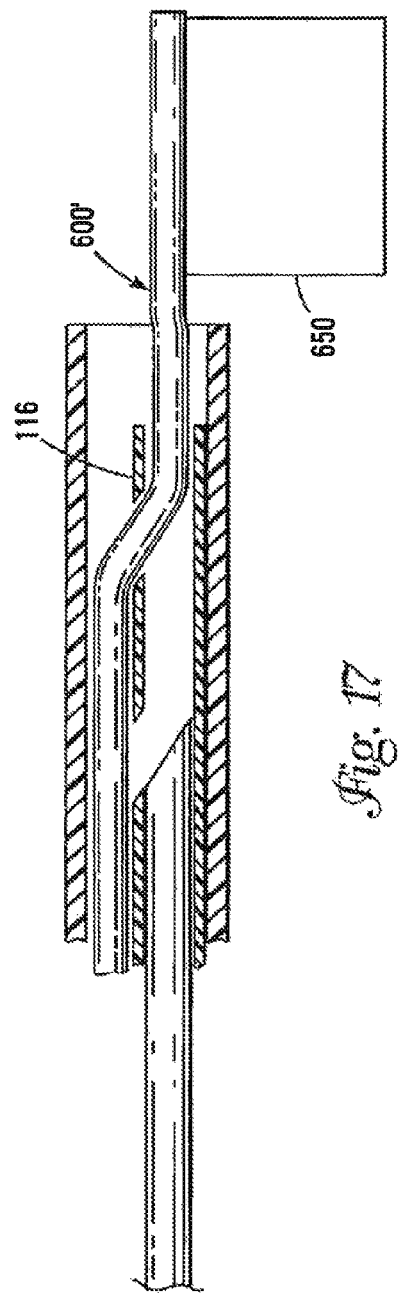

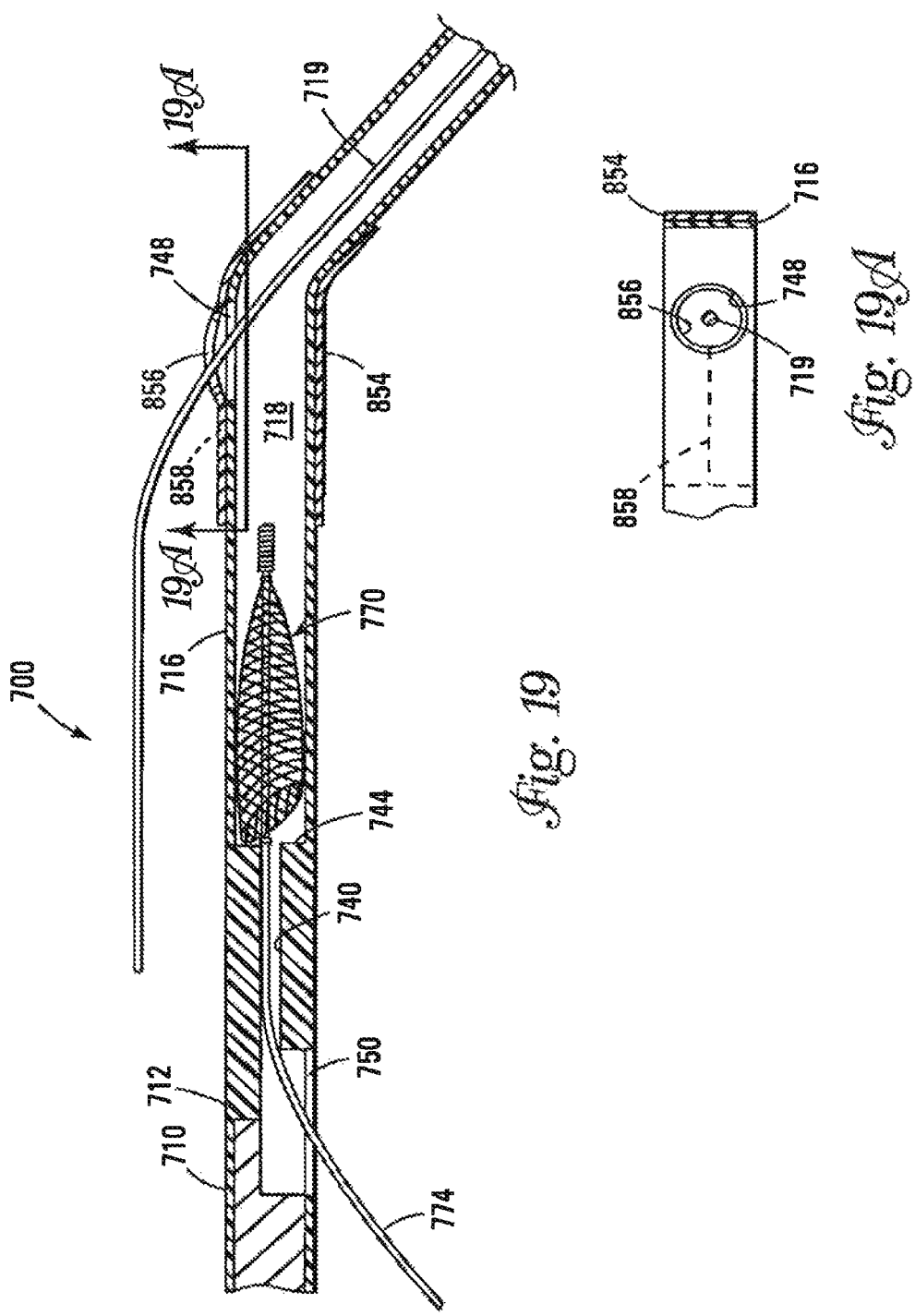

DOUBLE ENDED INTRAVASCULAR MEDICAL DEVICE

CROSS-REFERENCE TO RELATED APPLICATIONS

This application is a continuation of U.S. patent application Ser. No. 12/620,212, filed on Nov. 17, 2009, which is a continuation of U.S. patent application Ser. No. 10/810,445, filed on Mar. 26, 2004, now U.S. Pat. No. 7,637,920, which claims the benefit of, and priority to, U.S. Provisional Pat. Application Ser. Nos. 60/508,437 and 60/458,884, filed on Oct. 3, 2003 and Mar. 28, 2003, respectively, the entire content of each of the applications identified above being incorporated by reference herein.

FIELD OF THE INVENTION

The present invention is related generally to medical devices. More specifically, the present invention is related to intravascular medical devices such as catheters and guidewires.

BACKGROUND OF THE INVENTION

Blood vessel disease is a significant cause of premature disability and death. Heart attacks, strokes and other ailments are often caused by blood vessel disease.

The most common disease of the blood vessels is atherosclerosis. Atherosclerosis involves the accumulation of plaques of cholesterol, lipids and cellular debris within an artery. As the plaque accumulates, the artery wall thickens thereby narrowing the lumen of the artery. As the lumen narrows, the blood flow to tissue nourished by the artery is diminished. The development of plaques can also contribute to the formation of emboli or thrombi. An embolus is a moving obstruction such as a platelet aggregate. A thrombus can be a fixed obstruction such as a wall adherent blood clot or can become an embolus. A thrombus or embolus within a coronary artery can occlude the artery thereby causing myocardial infarction, angina and other conditions. A blockage caused by a thrombus or embolus within a vessel supplying blood to the brain can lead to a stroke. Renal, peripheral, and other blood vessels can also become blocked by an embolus or a thrombus thereby causing tissue damage downstream of the blockage.

A number of medical procedures have been developed to allow for the removal of plaque from vessel walls or to clear a channel through plaque, thrombus or clot to restore blood flow. For example, atherectomy or thrombectomy devices can be used to remove atheroma or thrombus. Vessel restrictions can also be treated with grafts that bypass the restrictions. Alternatively, balloon angioplasty and stenting procedures can be used to enlarge the lumen size of a vessel at an obstruction.

In a typical angioplasty procedure, a guide wire and guide catheter are inserted into a vessel of a patient. An inflatable balloon is then pushed through the guide catheter and advanced across a stenosis or blockage. Once positioned at the blockage, the balloon is inflated to dilate the blockage and open a flow channel through the partially blocked vessel region. One or more stents may also be placed across the dilated region or regions to reinforce the expanded vessel segment or to maintain dilatation of a vessel segment.

While some stenoses remain adherent to the vessel wall during treatment, others are more brittle, and may partially crack and fragment during treatment, allowing the fragments to flow downstream where they may block more distal and smaller vessels. Consequences of embolization include myocardial infarction, stroke, diminished renal function, and impairment of peripheral circulation possibly leading to pain and amputation.

Embolic protection devices have been developed to prevent the downstream travel of materials such as thrombi, grumous, emboli, and plaque fragments. Devices include occlusive devices and filters and may be deployed distal to a treatment site or proximal to a treatment site. Occlusive devices, for example distal inflatable balloon devices, can totally block fluid flow through the vessel. The material trapped by the inflatable devices can remain in place until removed using a method such as aspiration. Occlusive devices can also be deployed proximal to a treatment site and flow reversed or stopped at the treatment site. Following treatment emboli are carried by flow out of the vessel typically through a catheter and out of a patient. Filters can allow perfusing blood flow during the emboli capture process. The filters can be advanced downstream of a site to be treated and expanded to increase the filter area. Emboli, such as grumous or atheroma fragments, can be captured in the filter until the procedure is complete or the filter is occluded. When the capacity of the filter is reached, the filter may then be retracted and replaced.

Embolic protection devices can be delivered over guide wires and within guide catheters. The embolic protection methods are normally practiced ancillary to another medical procedure, for example angioplasty with stenting or atherectomy. The embolic protection procedure typically protects downstream regions from emboli resulting from practicing the therapeutic interventional procedure.

SUMMARY OF THE INVENTION

One inventive aspect of the present disclosure relates to a medical device comprising an elongated member configured to be advanced along a vascular path of a patient, the elongated member having opposite first and second ends, the first end and second ends both being adapted for intravascular insertion, and the first end having a different structure than the second end. The elongated member has sufficient flexibility to be advanced through a human vasculature. Preferably, the first and second ends are adapted to have different operating characteristics.

Depending on the operating characteristics needed for a particular procedure, a physician can insert either the first end portion or the second end portion of the elongated member into the patient's vasculature. The intravascular medical device can include any number of different types of devices used in the treatment of vascular disease. Example devices include guide wires, catheters, embolic protection device delivery systems and embolic protection device retrieval systems.

The invention provides a method for positioning a catheter within a patient's blood vessel, the method comprising: providing a catheter comprising an elongated member configured to be advanced along a vascular path of a patient, the elongated member having opposite first and second ends, the first end and second ends both being adapted for intravascular insertion, the first end comprising a delivery sheath, the second end comprising a retrieval sheath, the delivery sheath comprising at least one sidewall port adapted for receiving a wire, and the catheter having a lumen between the first end and the at least one sidewall port; providing a guide wire having a proximal end and a distal end; advancing the guide wire to a target site within the patient's blood vessel; and advancing the catheter over the guide wire by inserting the guide wire through the catheter lumen between the first end and the at least one sidewall port.

The invention provides a guide wire loading assist device comprising: a member having a proximal first and a distal second end and a lumen therebetween, the lumen being adapted to encase a catheter having a sidewall port adapted for receiving a wire; and a sidewall port in the member adapted for receiving a wire, wherein the lumen of the member has a first axial orientation from the proximal first end to the sidewall port of the member and a second axial orientation from the sidewall port of the member to the distal second end, the different axial orientations forming a bend in the lumen near the sidewall port, the sidewall port of the member being adapted to be coincident with the sidewall port of the catheter.

It is to be understood that both the foregoing general description and the following detailed description are exemplary and explanatory and are intended to provide further explanation of the invention as claimed.

BRIEF DESCRIPTION OF THE DRAWINGS

FIG. 7 shows the emboli protection device of FIG. 6 captured within the retrieval end of the catheter of FIG. 2.

FIG. 8 shows an alternative double-ended catheter.

FIG. 9 is a cross-sectional view taken along section line 9-9 of FIG. 8.

FIG. 10 shows another alternative double-ended catheter.

FIG. 11 is a cross-sectional view taken along section line 11-11 of FIG. 10.

FIG. 12 shows a double-ended catheter that includes an expandable balloon.

FIG. 12A is a detailed view of a portion of FIG. 12.

FIG. 12B is an alternative balloon catheter configuration.

FIGS. 16 and 17 show packaging techniques for protecting the delivery end of the catheter of FIG. 2 during shipping.

FIGS. 19 and 19A show a guide wire loading assist device disposed on an alternative double-ended catheter.

DETAILED DESCRIPTION OF THE INVENTION

Inventive aspects of the present disclosure relate to intravascular medical devices having opposite end portions each adapted for insertion within the vasculature of a patient. The opposite end portions each have different operating characteristics such that the medical device is capable of performing different functions depending upon the end of the device that is inserted into the patient. It will be appreciated that the broad aspects of the present invention are applicable to any number of different types of intravascular medical devices. Example devices include guide wires, catheters, implant delivery systems, emboli protection device delivery systems, implant retrieval systems, and emboli protection device retrieval systems.

With reference now to the various drawing figures in which identical elements are numbered identically throughout, a description is provided of embodiments that are examples of how inventive aspects in accordance with the principles of the present invention may be practiced. It will be appreciated that the depicted embodiments are merely exemplary, and are not intended to limit the broad scope of the present invention.

I. General Double Ended Device

Figure 1:
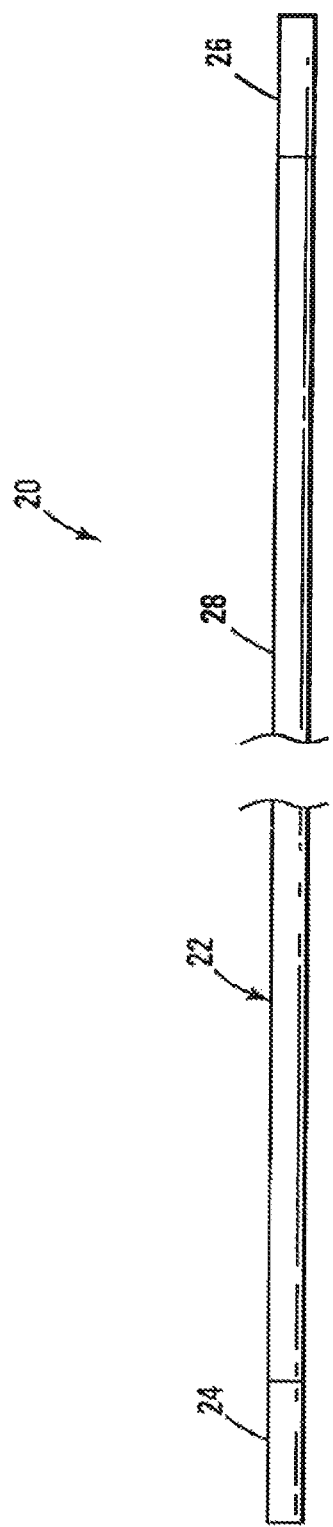
FIG. 1 schematically shows a medical device having features that are examples of inventive aspects in accordance with the principles of the present disclosure.

FIG. 1 illustrates an intravascular medical device 20 having features that are examples of inventive aspects in accordance with the principles of the present disclosure. It will be appreciated that the intravascular medical device 20 can be embodied in a number of different devices such as catheters, guide wires, embolic filter delivery devices, embolic filter retrieval devices, as well as other devices.

Referring to FIG. 1, the medical device 20 includes an elongated body 22 having first and second opposite end portions 24, 26. The elongated body 22 is preferably sufficiently flexible to allow the device to be advanced through a curving vascular pathway without kinking and without puncturing the vessel wall. The first and second end portions 24 and 26 are both capable of leading the elongated member 22 through the vasculature depending upon the direction the elongated member 22 is inserted into the vasculature. The first and second end portions 24 and 26 preferably have different operating characteristics. For example, in one embodiment, the first end portion 24 can be more flexible than the second end portion 26. In other embodiments, the first and second end portions 24 and 26 can have different pre-formed shapes adapted for facilitating advancement of the medical device 20 along different intravascular pathways. In still other embodiments, the first and second end portions 24 and 26 can be adapted for providing different functions. For example, in one embodiment, the first end portion 24 can be adapted for deploying an indwelling medical device such as a stent, graft or embolic protection device, and the second end portion 26 can be adapted for retrieving an indwelling medical device such as a stent, graft or embolic protection device.

The elongated member 22 of the medical device 20 includes a main body 28 that extends between the first and second end portions 24 and 26. The main body 28 can have any number of different types of configurations. For example, the main body 28 can have a solid configuration such as a solid wire configuration, a solid polymeric configuration, or a composite metal and polymeric configuration. In other embodiments, the elongated member 22 can have a tubular configuration defining a single lumen, or can define a plurality of lumens. In one embodiment, the main body 28 includes a metal having "super elastic" properties such as nitinol. The main body 28 can also include materials such as carbon fiber and its composites, liquid crystal polymers, ceramics, and composites in general. The elongated member may be coated with hydrophobic, hydrophilic, or biologically active coatings such as poly vinyl pyrrolidone coatings, ePTFE coatings, or heparin coatings. In one non-limiting embodiment, the elongated member 22 has a length L in the range of 60-300 cm, and an outer diameter D in the range of 0.013" to 0.100" (0.033 to 0.25 cm).

The end portions 24 and 26 of the medical device can have any number of different configurations. For example, end portions 24 and 26 can include a polymeric material, a metal material, a combined polymer and metal material, a shape memory material, or a super elastic material. Further, the end portions 24, 26 can include a solid configuration, or a tubular configuration defining a single lumen or a multi-lumen configuration. Moreover, the end portions 24 and 26 can include constant diameter embodiments, tapered diameter embodiments, solid wall tubular embodiments, perforated wall tubular embodiments, slotted-wall tubular embodiments, coiled embodiments, and any number of other different configurations. The first and second end portions 24 and 26 can be unitary parts of the main body 28, or can be separate pieces or components that are affixed to the main body 28. It will be appreciated that the lengths and diameters of the end portions 24, 26 will vary depending upon their desired operating characteristics. In one embodiment, the end portions 24, 26 function as flexible guide tips having greater flexibility than the main body 28, and different flexibilities from one another.

II. Double Ended Catheter with Rapid Exchange Features

Figure 2:
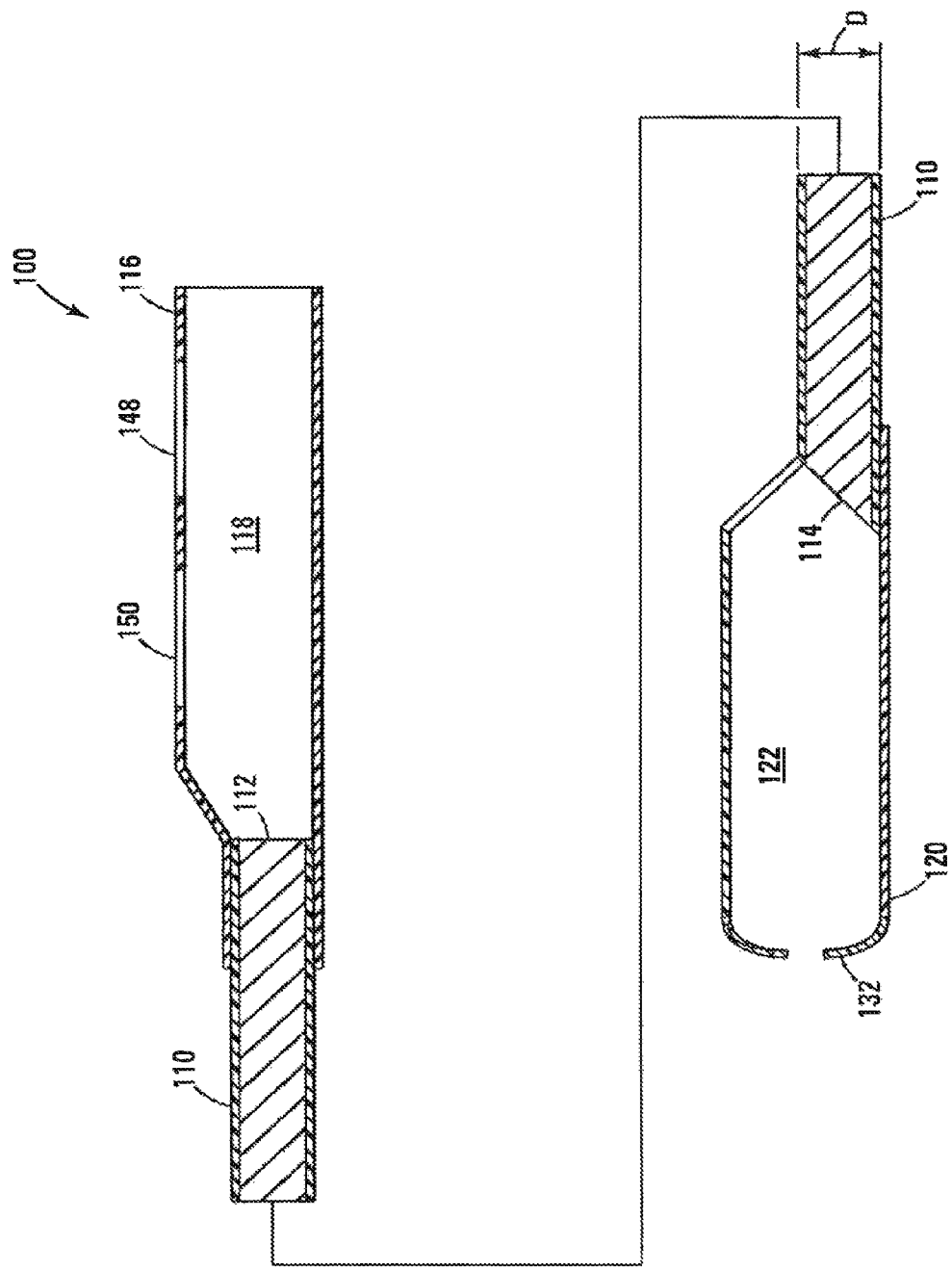
FIG. 2 shows a double-ended catheter having features that are examples of inventive aspects in accordance with the principles of the present disclosure.

FIG. 2 illustrates a catheter 100 having features that are examples of inventive aspects in accordance with the principles of the present disclosure. The catheter 100 includes a central shaft 110 having a first end 112 positioned opposite from a second end 114. A tip in the form of a flexible delivery sheath 116 is positioned at the first end 112. The flexible delivery sheath 116 defines an internal pocket 118 (i.e., a compartment, cavity, enclosure, chamber or receptacle) configured for receiving a preloaded device (e.g., a preloaded embolic protection device such as the filter device 70 shown in FIGS. 3-5). The catheter 100 also includes a flexible retrieval sheath 120 positioned at the second end 114 of the shaft 110. The flexible retrieval sheath 120 defines an internal pocket 122 sized and shaped for receiving a medical device (e.g., an embolic protection device such as the filter device 70 of FIGS. 3-5) for retrieval of the medical device after the device has been used.

The shaft 110 of the catheter 100 is preferably sufficiently flexible and has sufficient column strength to be advanced through the vasculature of a patient. In a preferred embodiment, the shaft 110 includes a solid wire coated with an outer layer of a polymeric material. However, it will be appreciated that in other embodiments, the shaft could include a tubular metal configuration or other configurations. In one non-limiting embodiment adapted for use in coronary applications, the shaft 110 can have a length in the range of 70-170 cm, and more preferably in the range of 100-140 cm. In certain embodiments, the shaft 110 can have an outer diameter D in the range of 0.026"-0.040" (0.066-0.10 cm).

Referring still to FIG. 2, the delivery sheath 116 of the catheter preferably includes a material that is softer and more pliable than the central shaft 110. The flexible design of the delivery sheath 116 facilitates advancing the catheter 100 through tortuous vessels while the more rigid central shaft 110 can provide pushability. In a preferred embodiment, the delivery sheath 116 is formed of a polymer such as LDPE, MDPE, or PEBAX. In one embodiment, the outer diameter of the delivery sheath can be in the range of 0.026-0.040 inches (0.066-0.10 cm), a wall thickness of the delivery sheath can be in the range of 0.001 to 0.005 inches (0.0025 to 0.013 cm), and a length of the delivery sheath can be in the range of 10 to 40 centimeters.

Referring still to FIG. 2, the delivery sheath 116 includes a first sidewall port 148 and a second sidewall port 150. The first and second sidewall ports 148, 150 are spaced apart from one another along the length of the sheath 116. The first sidewall port 148 is located closer to a free end of the sheath 116 than the second sidewall port 150. The ports 148, 150 are preferably skived and dimensioned to allow a distally and inwardly extending wire to extend from the outside of the sheath 116 to the internal pocket 118 at an angle of less than about 10° relative to a longitudinal axis of the catheter 100. Further details regarding the configuration of the flexible sheath can be found in U.S. Patent Application Publication No. 2003/0233117 A1, published Dec. 18, 2003, entitled RAPID EXCHANGE CATHETERS USABLE WITH EMBOLIC PROTECTION DEVICES, the contents of which are hereby incorporated by reference herein.

The recovery sheath 120 of the catheter 100 is preferably made of a compliant material that is more flexible than the shaft 110. Preferably, the sheath 120 has sufficient flexibility to allow the sheath 120 to traverse the tortuous pathways typically encountered within the vasculature of a human. Suitable materials for making the sheath 120 include thermal plastic polymers, polymer blends and thermal set polymers such as silicone, or silicone blends with a low durometer. One such material is a 35/40 D PEBAX blend. Any other appropriate compliant materials may, however, be used. In one embodiment, the outer diameter of the recovery sheath can be in the range of 0.040-0.060 inches (0.10 to 0.15 cm), a wall thickness of the recovery sheath can be in the range of 0.001 to 0.005 inches (0.0025 to 0.013 cm), and a length of the recovery sheath can be in the range of 5 to 30 centimeters.

Referring still to FIG. 2, the recovery sheath has an outermost end that forms a rolled tip 132. The rolled tip 132 is especially designed for crossing a stented or otherwise constricted region of a blood vessel. The rolled tip 132 can also function to capture an implanted device such as an embolic protection device. Further details regarding the recovery sheath 120 can be found in U.S. Patent Application Publication No. 2002/0111649 A1, published Aug. 15, 2002, entitled ROLLED TIP RECOVERY CATHETER, the contents of which are hereby incorporated by reference herein.

In certain embodiments, the sheaths 116, 120 can include one or more bands of radiopaque material, or can be filled with radiopaque material. Examples of radiopaque materials include barium sulfate, bismuth sub carbonate, tungsten powder, and the like. The presence of radiopaque materials facilitates viewing the sheaths under fluoroscopy. The sheaths 116, 120 may be coated with hydrophobic, hydrophilic, or biologically active coatings such as poly vinyl pyrrolidone coatings, ePTFE coatings, or heparin coatings.

Use of the catheter 100 will now be described with respect to a coronary procedure. However, it will be appreciated that the embodiment can also be used for treating other vessels (e.g., carotid, renal, peripheral, and other blood vessels).

In an example of a coronary procedure, a physician first inserts a guidewire (not shown) into the femoral artery of a patient near the groin, and advances the guidewire through the artery, over the aorta and to a coronary ostium 21. Once the guidewire is in place, a guide catheter 11 is passed over the guidewire and advanced until a distal end of the guide catheter 11 is located adjacent the coronary ostium 21. The guidewire (not shown) is then removed. With the guide catheter 11 in place, a coronary guidewire 19 is inserted into the guide catheter and advanced into the coronary artery. See FIG. 3. Next, the proximal end of the coronary guidewire 19 is inserted (i.e. back-loaded) through the distal opening of sheath 116 and then the first sidewall port 148 of the delivery catheter 100.

Figure 3:
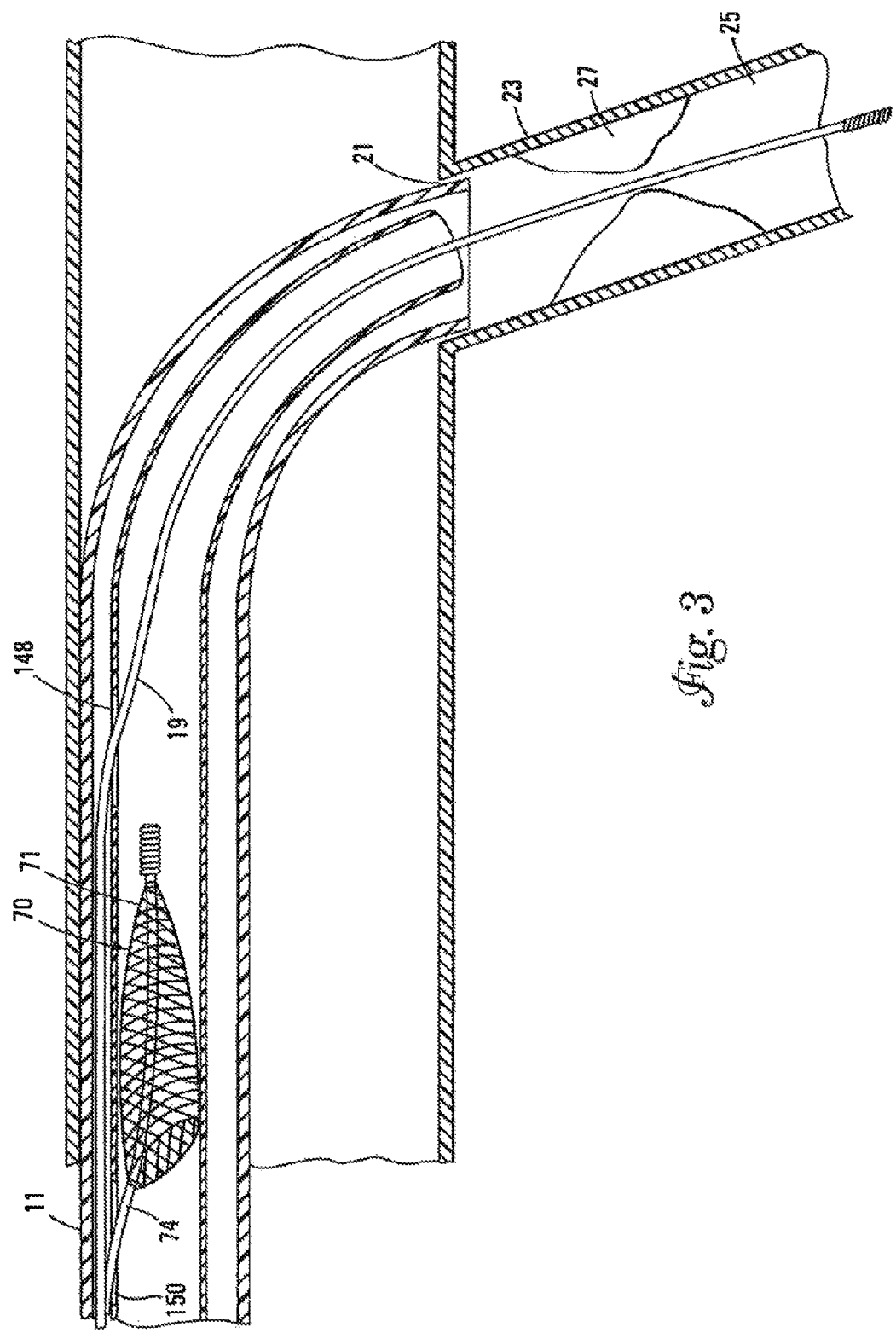
FIG. 3 shows the catheter of FIG. 2 with a delivery end of the catheter containing an emboli protection device, the delivery end is located adjacent to an ostium.

Prior to insertion of the coronary guidewire 19 through the first sidewall port 148, an embolic protection device such as an embolic filter device 70 is preferably pre-loaded within the delivery sheath 116 of the catheter 100. The filter device 70 is preferably a self-expandable filter device such as the filter device disclosed in U.S. Pat. No. 6,325,815, the contents of which are hereby incorporated by reference herein. The filter device 70 includes an expandable filter mesh 71 secured to the distal end of a host wire 74. As shown in FIG. 3, in the pre-loaded configuration, the mesh of the filter device is compressed in a radially reduced profile configuration within the delivery sheath 116, and the host wire 74 extends from the mesh material through the second sidewall port 150 of the delivery sheath 116. The filter device 70 can be viewed as one type of distal emboli protection element. Other distal protection elements which can be included as part of the device are occlusive emboli protection elements, including expandable or inflatable elements for blocking fluid flow through a vessel.

Figure 4:
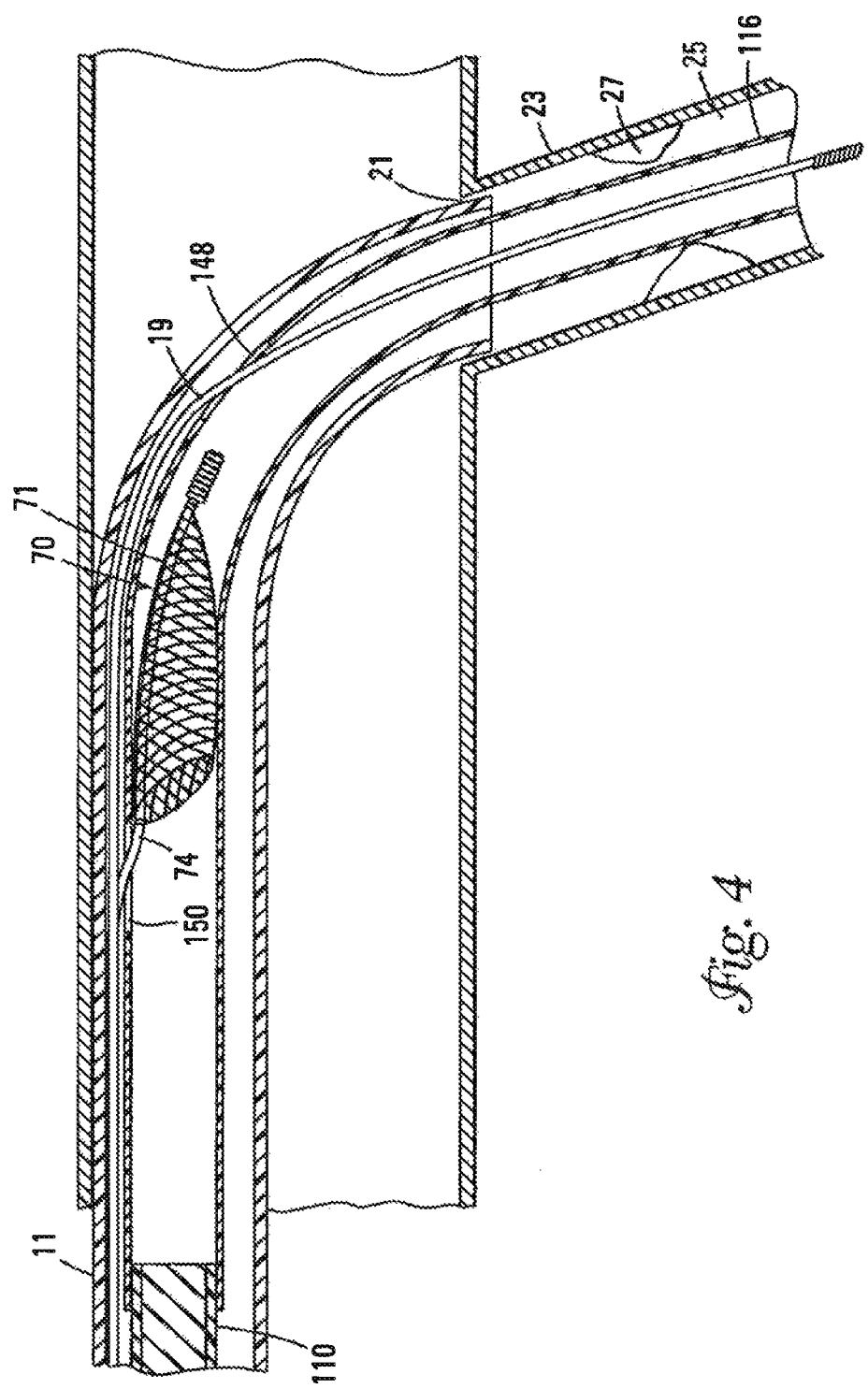
FIG. 4 shows the delivery end of the catheter of FIG. 2 at a target site.

After the guide wire 19 has been back-loaded through the delivery sheath 116, the delivery sheath 116 of the catheter 100 is advanced through the guide catheter 11 along the guidewire 19 until the delivery sheath 116 is advanced to the distal tip the guide catheter 11, as shown in FIG. 3. Preferably, the guidewire 19 is then further advanced within the coronary artery to a point where the distal most tip of the guidewire 19 is located at a target site 25 within a coronary artery 23, (e.g., a site located downstream of a treatment site such as an occlusion 27). The delivery sheath 116 of the catheter 100 can then be tracked along the guide wire 19 to the target site 25 as shown in FIG. 4. In other methods, the guidewire 19 and the catheter 100 can be advanced together across the target site with the guidewire 19 providing stiffening for the catheter 100.

Figure 5:
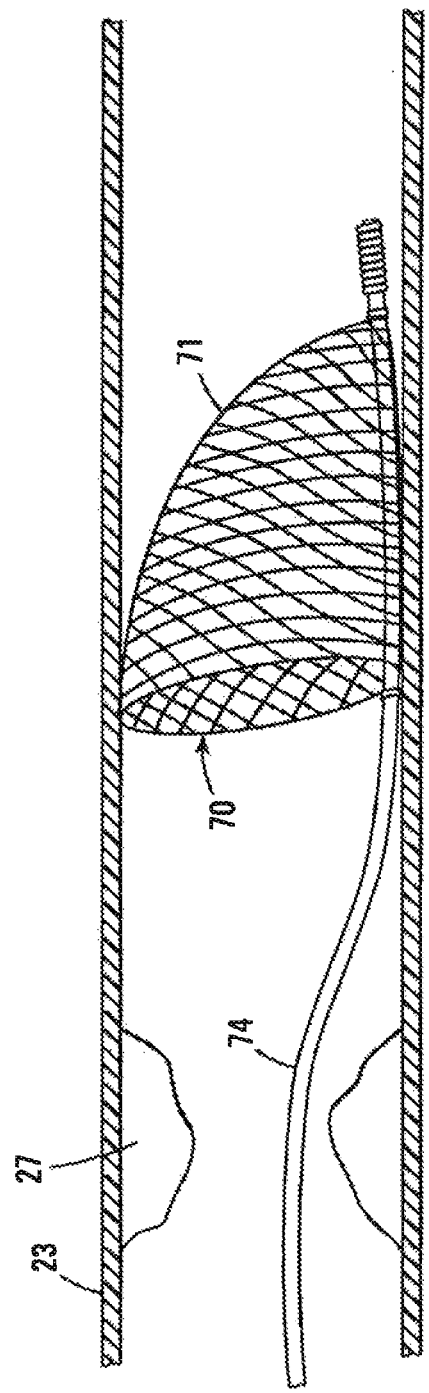
FIG. 5 shows the emboli protection device of FIGS. 3 and 4 deployed at the target site.

Once the tip of the delivery sheath 116 is located at the target site 25, the guidewire 19 is retracted proximally through the distal sidewall port 148. With the guidewire no longer present within the delivery sheath 116, the filter device 70 can be distally advanced to the tip of the delivery sheath 116 and then from the delivery sheath 116. For example, the embolic filter 70 can be advanced from the sheath 116 by proximally retracting the catheter 100 while the host wire 74 is held in place by the treating physician. By retracting the catheter 100, the sheath 116 retracts relative to the filter device 70 thereby exposing the filter device 70 and allowing the filter device 70 to expand radially so as to provide filtration across the entire cross sectional area of the vessel as shown in FIG. 5.

Once the filter device 70 is in place, the catheter 100 can be retracted from the patient, and an interventional device (e.g., a balloon angioplasty catheter, a stent delivery catheter, an atherectomy device, a thrombectomy device or any other device) can be introduced over the host wire 74 and used to treat the treatment site. As the treatment site is treated, any emboli generated during the treatment process are captured by the filter 70.

Figure 6:
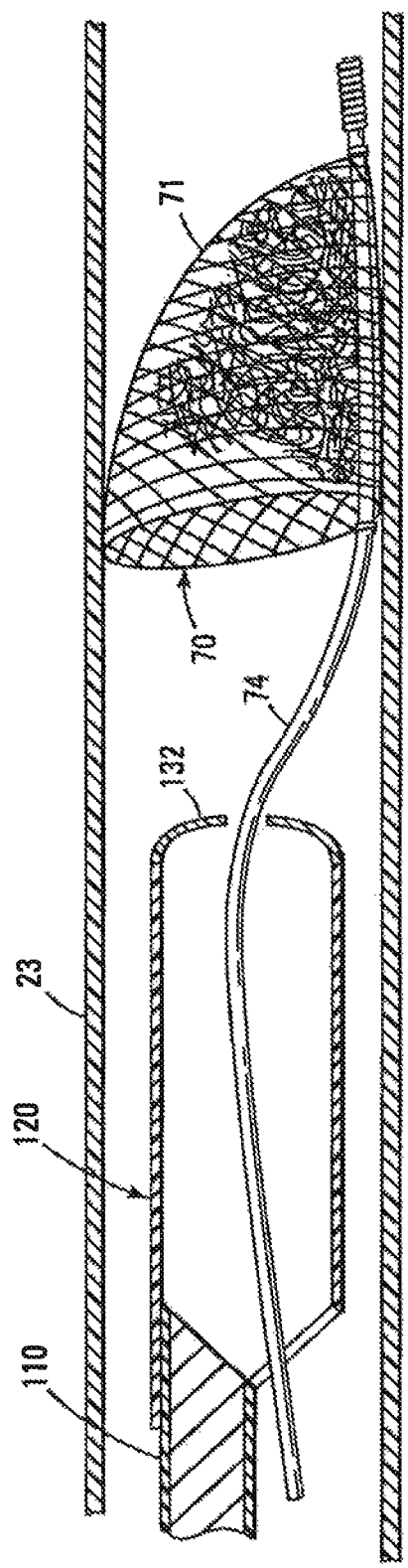
FIG. 6 shows the catheter of FIG. 2 with a retrieval end of the catheter in close proximity to the deployed emboli protection device of FIG. 5.

After the treatment process has been completed, the interventional device is removed and the catheter 100 is reintroduced over the host wire 74. However, when reintroduced, the catheter 100 is reversed such that the recovery sheath 120 functions as the distal most tip of the catheter 100. Preferably, the host wire 74 is passed through the interior of the recovery sheath 120 as shown in FIG. 6. The catheter 100 is advanced until the rolled end 132 is positioned immediately proximal to the filter device 70. The host wire 74 is then pulled in a proximal direction causing a proximal end of the filter device 70 to contact the rolled tip 132. As the filter device 70 contacts the rolled tip 132, the rolled tip 132 is urged elastically toward an open orientation in which the filter device 70 can be passed into the recovery sheath 120. Once the filter device 70 has been fully drawn into the sheath 120 as shown in FIG. 7, the rolled tip 132 reaches a point where it ceases to be engaged by the filter device 70, and it elastically returns to its undeflected configuration. It will be appreciated that the resilient material forming the sheath 120 prevents the escape of emboli when the filter device 70 is captured. Preferably, at least a portion of the wall of the sheath 120 closely encompasses the periphery of the filter device 70 and assumes the shape of the periphery. As a result, emboli are prevented from passing between the periphery of the filter device 70 and the wall of the sheath 120. Alternatively, the filter device 70 can be partly drawn into the recovery sheath 120 such that only the enlarged proximal opening of the filter is within the sheath.

Once the filter device is positioned within the recovery sheath 120, both the host wire 74 and the catheter 100 can be withdrawn from the patient together as a unit. Thereafter, the procedure is completed by removing the guide catheter 22 from the patient.

III. Over-the-Wire Double Ended Catheter

FIGS. 8 and 9 illustrate an alternative catheter 200 having a similar configuration as the catheter 100 of FIG. 2, except the solid central shaft 110 has been replaced with a double lumen configuration 210 having a first end 212 and a second end 214. The catheter 200 includes a delivery sheath 116 positioned at the first end 212 and a recovery sheath 120 positioned at the second end 114. The double lumen configuration 210 includes a first tube 211 that is coaxial with the delivery sheath 116, and a second tube 213 that is coaxial with the recovery sheath 120. It will be appreciated that the tubes of the double lumen configuration 210 are coupled together and are sufficiently flexible to be able to be passed through a tortuous vascular pathway, and also have sufficient column stiffness to allow the catheter 200 to be pushed through the vasculature. It will be appreciated that the tubes can be manufactured using any number of known techniques. For example, the tubular structures may be extruded or coextruded in the cross sectional shape shown in FIG. 9 or in any number of alternative cross sections, for example those known in the art as double D, smile, or other configurations. Alternatively, the tubular structures can be manufactured from individual tubes of polymer such as polyimide or a super elastic material such as nitinol and held together with adhesives or a thin tube that surrounds both single lumen tubes. It will be appreciated that any number of different types of material can be used to form double lumen configuration 210.

Similar to the previous embodiment, the catheter 200 can be used to both deliver a device such as an embolic protection device, and to retrieve a device such as an embolic protection device. The catheter 200 is used in a manner similar to the catheter 100, except the catheter 200 does not have rapid exchange capabilities. Instead, when the catheter 200 is used with the delivery sheath 116 as the distal end, a guidewire is passed through the entire length of the first tube 211. Similarly, when the retrieval sheath 120 is used as the distal end of the catheter 200, a guidewire or wire such as host wire 74 is passed completely through the second tube 213 of the double lumen configuration 210.

IV. Double Ended Catheter with Combined Rapid Exchange and Over-the-Wire Configuration FIGS. 10 and 11 illustrate another catheter 300 having features that are examples of inventive aspects in accordance with the principles of the present disclosure. Similar to the previous embodiments, the catheter 300 includes a delivery sheath 116 positioned at one end, and a recovery sheath 120 positioned at the opposite end. The delivery sheath 116 and the recovery sheath 120 are interconnected by an elongated central structure 310 that includes a solid shaft 350 coupled to a tubular shaft 352. The solid shaft 350 is connected to the recovery sheath 120, and the tubular shaft 352 is connected to the delivery sheath 116. The elongated central structure is sufficiently flexible to bend through the contours of a tortuous vascular pathway, and also include sufficient column strength to allow the catheter 300 to be pushed through the pathway. The tubular shaft structure 352 has a central lumen in fluid communication with the pocket 118 of the delivery sheath 116.

It will be appreciated that the catheter 300 can be used to deliver devices such as embolic protection devices in much the same way as the previous two embodiments. However, when delivering an embolic protection device using the delivery sheath 116, the delivery sheath 116 as well as the entire tubular shaft 352 would typically be passed over a guidewire. In contrast, when the catheter 300 is used as a retrieval device, the catheter 300 can be used as a rapid exchange catheter in which a guidewire or wire is not passed through the entire catheter, but instead only passes through the distal tip (e.g., the recovery sheath portion 120 of the catheter).

V. Double Ended Catheter with Balloon

FIG. 12 shows another catheter 400 having features that are examples of inventive aspects in accordance with the principles of the present disclosure. The catheter 400 includes a delivery sheath 116 positioned at one end and a recovery sheath 120 positioned at the opposite end. The delivery sheath 116 and the recovery sheath 120 are interconnected by a central elongated member 410. The elongated member 410 includes a solid shaft 411 connected to the recovery sheath 120, and a tubular shaft 413 connected to the delivery sheath 116. The tubular shaft 413 defines a central lumen 415 that extends from a first end 417 of the tubular shaft to the delivery sheath 116. The lumen is preferably sealed so as to not be in fluid communication with the interior of the delivery sheath 116. The delivery sheath 116 includes a guidewire port 148 and a host wire port 150.

Referring still to FIG. 12, a balloon such as an angioplasty balloon or a low pressure occlusion balloon 419 is provided on the tubular shaft 413 adjacent to the delivery sheath 116. The balloon 419 is in fluid communication with the lumen 415 of the tubular shaft 413. The first end 417 of the tubular shaft 413 is sealed by a septum or other seal 421. The septum or seal 421 can include multiple membranes 421a, 421b (see FIG. 12A) bonded together at a perimeter of the membranes. The membrane 421a can have a self-closing slit 425 while membrane 421b can have a central hole that seals against a blunt needle. Either membrane can have a rim 427 that can be sealed to lumen 415 of tubular shaft 413. A syringe with a blunt needle can be used to inject fluid into the lumen through the seal 421 to inflate the balloon 419.

Other techniques can also be used to provide fluid into the lumen. For example, the first end 417 of the tubular shaft 413 can include a side port in fluid communication with a Luer fitting. The Luer fitting provides a connection location for attaching an inflation device. Tuohy Borst fittings can be secured to the tubular shaft at locations distal to and proximal to the side port to provide a seal between the Luer fitting and the catheter body. The Tuohy Borst fittings can also referred to as hemostatic valves.

Figure 13:
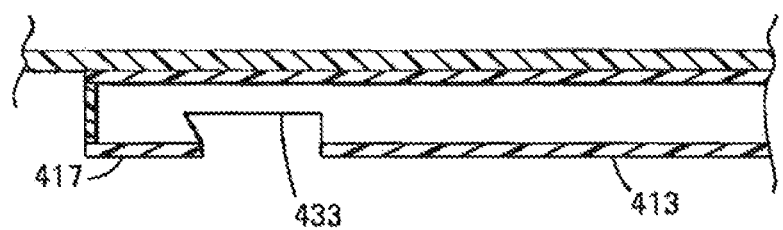
FIGS. 13-15 show a technique for equipping the catheter of FIG. 12 with a Luer fitting for use in inflating and deflating the expandable balloon.
Figure 14:
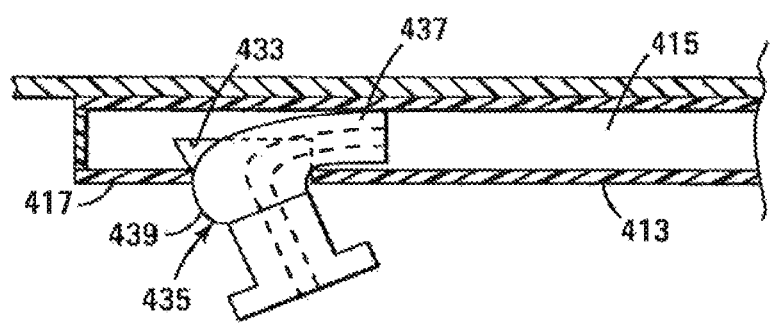
Figure 15:
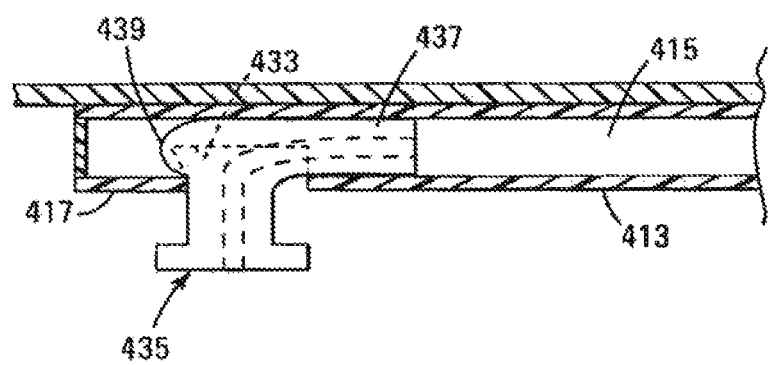

Additionally, a Luer lock fitting can be used to provide fluid to the lumen 415. For example, as shown in FIG. 13, the tubular shaft 413 can include an elongated slot 433 adjacent the first end in which a Luer lock fitting 435 (shown in FIGS. 14 and 15) can be inserted. FIG. 14 shows the Luer lock fitting 435 partially inserted within the slot 433. A stem 437 of the lock fitting 435 fits within the lumen 415. Preferably, the stem 437 snugly fits within the lumen 415 such that friction between the stem 437 and the wall of the tubular shaft 413 function to provide a fluid tight seal about the stem 437. A rounded end 439 of the lock fitting 435 also fits within the slot 433 such that the Luer fitting 435 snaps into a locked or seated position as shown in FIG. 15. The Luer fitting 435 provides an attachment location for attaching a balloon inflation apparatus to the catheter.

It should also be appreciated that the balloon shown in FIG. 12 could alternatively be positioned on the delivery sheath 116 of catheter 400 by those skilled in the art. See, for example, FIG. 12B.

The catheter of FIG. 12B can be used in a manner that helps to prevent distal migration of emboli during embolic filter passage across a treatment site. For example, the catheter can be used as described for catheter 100 in connection with FIGS. 3-7. However, the catheter is preloaded with an actuator style embolic protection device such as that described in U.S. Pat. No. 6,520,978 B1, the contents of which are hereby incorporated by reference herein. Prior to crossing the treatment site, the catheter balloon 419 is inflated to a pressure sufficient to substantially impede blood flow across the treatment site. After balloon inflation, the guidewire 19 is withdrawn and the embolic filter is advanced across the treatment site in a collapsed diameter. Importantly, emboli liberated by the embolic filter during treatment site passage cannot be transported distally because the inflated balloon 419 prevents distal blood flow and distal transport of emboli within the flow stream. After crossing the treatment site, the actuating style filter is actuated to cause it to diametrically enlarge and position the filter across the vessel cross sectional area. At this point, the balloon 419 is deflated and flow is restored, causing emboli liberated during treatment site crossing to be transported to and captured by the filter. The catheter can now be removed and the treatment site treated. Alternatively, the catheter can be advanced and the balloon used to treat a lesion, followed by balloon deflation and capture of released emboli in the filter.

While a balloon has been shown, it will be appreciated that in alternative embodiments, the catheter could include openings for delivering a substance (e.g., a medicine, dye, or other substance) to the vasculature of a patient.

VI. Protective Packaging

FIG. 16 illustrates a system 600 for protecting the delivery sheath 116 during shipping. The system includes an outer protective sheath 610 mounted over the exterior of the delivery sheath 116. A stylette 615 extends into the tip of the delivery sheath 116, through the first sidewall port 148 and along the outer surface of the catheter. The stylette provides rigidity for protecting the delivery sheath 116. A loop 620 is provided for pulling the stylette 615 from the sheath 116.

FIG. 17 shows an alternative stylette 600' having a flag 650 as compared to a loop 620. Method of use instructions for the catheter can be printed on the flag 650.

Alternatively the protective packaging can be applied to the recovery sheath 120, or to both the delivery sheath 116 and the recovery sheath 120. It will be further appreciated that it is not necessary to utilize both a stylette and protective sheath; they can be used alone as well as in combination at either or both ends of the catheter.

VII. Double Ended Catheter with Rapid Exchange Features and Variable Diameter

Figure 18:
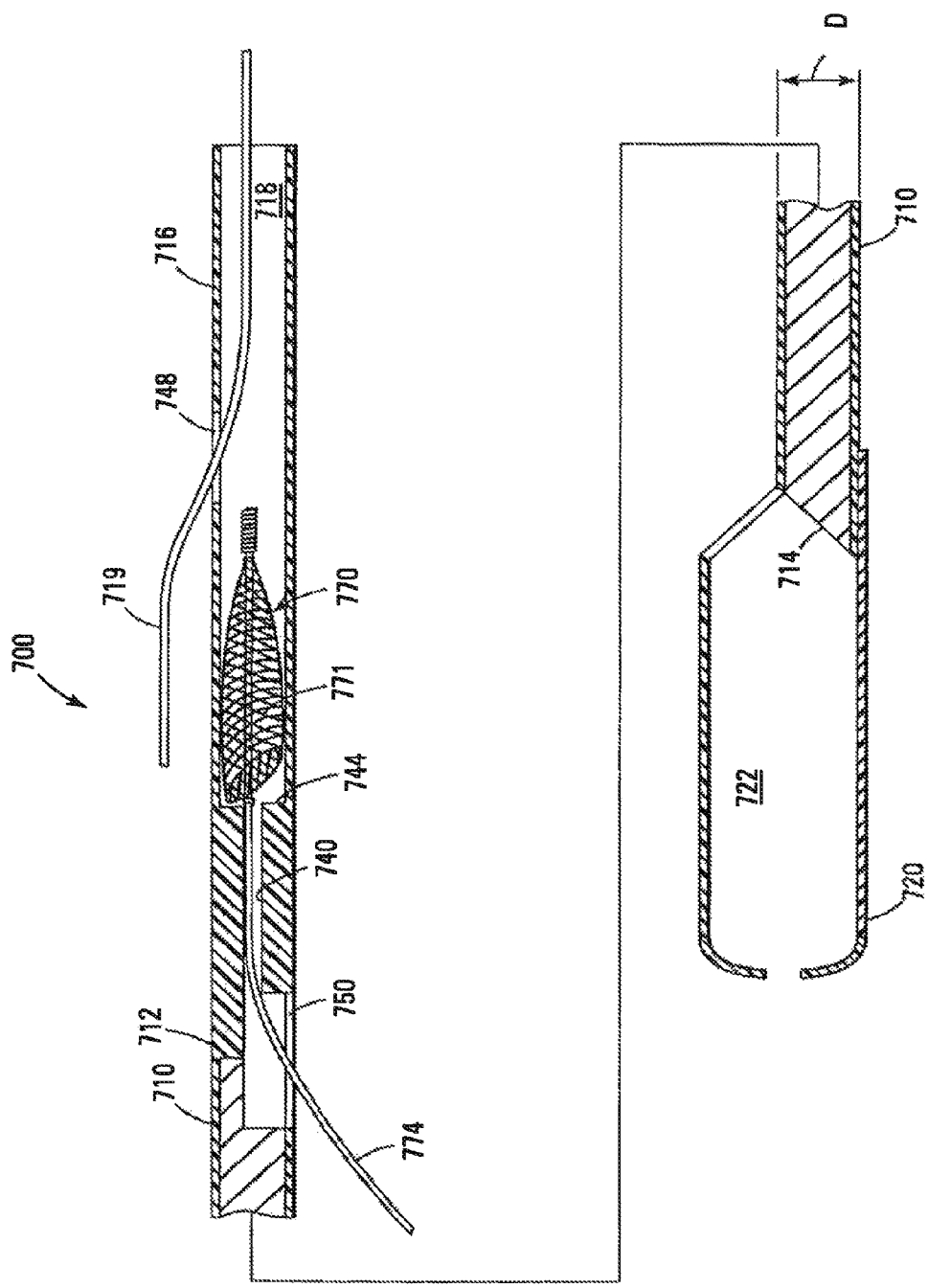
FIG. 18 shows an alternative double-ended catheter.

FIG. 18 illustrates a catheter 700 similar to the catheter of FIG. 2. The catheter 700 includes a central shaft 710 having a first end 712 positioned opposite from a second end 714. A tip in the form of a flexible delivery sheath 716 is positioned at the first end 712. The flexible delivery sheath 716 defines an internal pocket 718 (i.e., a compartment, cavity, enclosure, chamber or receptacle) configured for receiving a preloaded device (e.g., a preloaded embolic protection device such as the filter device 770 shown in FIG. 18). The filter device 770 includes an expandable filter mesh 771 secured to the distal end of a host wire 774. The catheter 700 also includes a flexible retrieval sheath 720 positioned at the second end 714 of the shaft 710. The flexible retrieval sheath 720 defines an internal pocket 722 sized and shaped for receiving a medical device (e.g., an embolic protection device such as the filter device 770 of FIG. 18) for retrieval of the medical device after the device has been used.

The delivery sheath 716 includes a first sidewall port 748 and a second sidewall port 750. The first and second sidewall ports 748, 750 are spaced apart from one another along the length of the sheath 716. The first sidewall port 748 is located closer to a free end of the sheath 716 than the second sidewall port 750. The ports 748, 750 are preferably skived and dimensioned to allow a distally and inwardly extending wire to extend from the outside of the sheath 716 to the internal pocket 718 at an angle of less than about 10° relative to a longitudinal axis of the catheter 700.

The catheter 700 includes a lumen portion 740 of a narrower diameter than the internal pocket 718. The diameter of the internal pocket 718 is reduced at constriction 744. Constriction 744 prevents proximal movement of the filter device 770 and creates a preloading stop or "holding zone" location for the filter device 770. This location is distal of the constriction 744 and proximal of the first sidewall port 748 to prevent interaction of the guidewire 719 with the filter 770.

VIII. Guide Wire Loading Assist Device

FIGS. 19 and 19A illustrate a guide wire loading assist device 854. The device 854 has a port 856 that lines up with sidewall port 748 of catheter 700. As shown in FIG. 19, assist device 854 bends catheter 700 to make loading of the guide wire 719 easier. In some embodiments the assist device 854 bends catheter 700 by having a pre-formed shape and stiffness sufficient to overcome the shape and stiffness of catheter 700. Specifically, the device 854 ensures that the guide wire will exit the correct port without interacting with the filter 770.

The device 854 may be loaded prior to packaging or provided as a separate piece within the packaging for the physician to place on the catheter 700 prior to introducing the guide wire 719. A slit 858 that runs from port 856 to the proximal end of the device 854 allows for easy removal of the device once the guide wire is in place. Alternatively, a slit may run from port 856 to distal end of the device 854, or both proximal and distal slits may be provided. In some embodiments, slots are used rather than slits. In another embodiment a pull tab of a size sufficient for a device user to grasp is provided at one or both ends of device 854 for the purpose of facilitating device 854 removal from catheter 700. In some embodiments the device 854 is comprised of a polymer having bright color so as to facilitate rapid identification by the device user. After the device 854 is removed, the catheter reverts to its original conformation.

The device 854 preferably is made of a heat formable material formed with a slight bend. Suitable heat formable materials include polymers such as LDPE, MDPE, and PEBAX. The device 854 can also be injection molded.

Figure 19B:
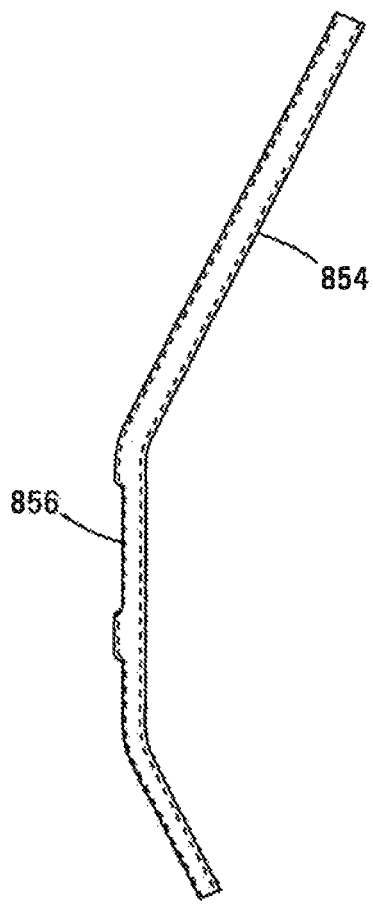
FIGS. 19B and 19C show an alternate embodiment of a guide wire loading assist device.
Figure 19C:
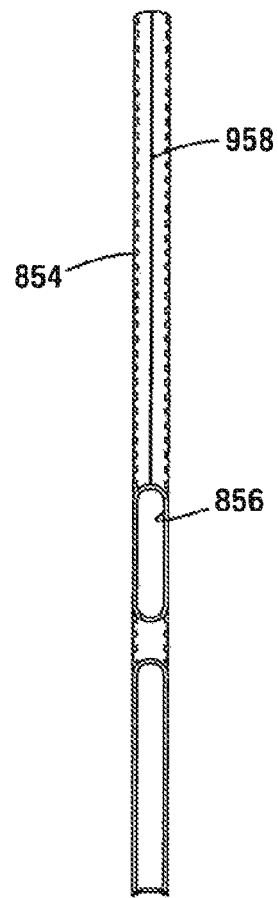

FIGS. 19B and 19C illustrate an alternate embodiment of a guide wire loading assist device 854. The device 854 has a port 856 that lines up with sidewall port 748 of catheter 700. As shown in FIG. 19, assist device 854 bends catheter 700 to make loading of the guide wire 719 easier. In some embodiments the assist device 854 bends catheter 700 by having a pre-formed shape and stiffness sufficient to overcome the shape and stiffness of catheter 700. Specifically, the device 854 ensures that the guide wire will exit the correct port without interacting with the filter 770.

The device 854 may be loaded prior to packaging or provided as a separate piece within the packaging for the physician to place on the catheter 700 prior to introducing the guide wire 719. A slit 958 runs from port 856 to the distal end of the device 854 and allows for easy removal of the device once the guide wire is in place. A slot runs from a location proximal to port 856 to a proximal end of the device 854. The axis of proximal slotted end of device 854 is oriented approximately 25° away from the axis of the device 854 in the region of port 856. The proximal slotted end of device 854 functions as a pull tab of a size sufficient for a device user to grasp for removal of device 854 from catheter 700. In some embodiments the device 854 is comprised of a polymer having bright color so as to facilitate rapid identification by the device user. After the device 854 is removed, the catheter reverts to its original conformation.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

The invention claimed is:

1. A catheter comprising:
 an elongated member defining a longitudinal axis, and having opposite first and second end portions;
 a delivery sheath connected to the first end portion of the elongated member, the delivery sheath including a first internal cavity configured to receive a vascular device; and
 a retrieval sheath connected to the second end portion of the elongated member, the retrieval sheath including a second internal cavity configured to receive the vascular device, the delivery sheath and the retrieval sheath being connected to the elongated member such that the catheter is formed as a single, unitary structure; wherein the delivery sheath is fixed to the first end portions of the elongated member, and the retrieval sheath is fixed to the second end portion of the elongate member.

2. The catheter of claim 1, wherein the delivery sheath includes a first sidewall port configured to receive a wire.

3. The catheter of claim 2, wherein the delivery sheath further includes a second sidewall port configured to receive the wire, the second sidewall port being spaced longitudinally from the first sidewall port.

4. The catheter of claim 3, wherein the first and second sidewall ports are in circumferential alignment.

5. The catheter of claim 3, wherein the first and second sidewall ports are skived.

6. The catheter of claim 5, wherein the first and second sidewall ports are configured to receive the wire such that the wire subtends an angle less than 10° with respect to the longitudinal axis.

7. The catheter of claim 1, wherein the elongated member includes an outer wall defining a lumen extending through the elongated member.

8. The catheter of claim 7, wherein the first internal cavity of the delivery sheath defines an internal transverse cross-sectional dimension greater than an internal transverse cross-sectional dimension defined by the lumen extending through the elongated member.

9. The catheter of claim 8, wherein the second internal cavity of the retrieval sheath defines an internal transverse cross-sectional dimension larger than the internal transverse cross-sectional dimension defined by the lumen extending through the elongated member.

10. The catheter of claim 1, wherein the retrieval sheath includes a rolled tip extending inwardly toward a central longitudinal axis defined by the elongated member.

11. The catheter of claim 1, wherein the elongated member comprises a first material, the first material being of sufficiently rigidity and flexibility to facilitate advancement of the catheter through a patient's vasculature.

12. The catheter of claim 11, wherein the delivery sheath comprises a second material different than the first material.

13. The catheter of claim 12, wherein the retrieval sheath comprises the second material.

14. The catheter of claim 13, wherein the second material is more pliable than the first material.

15. The catheter of claim 1, wherein the delivery sheath and the retrieval sheath each include at least one radiopaque portion.

16. The catheter of claim 1 further including a hydrophobic coating, a hydrophilic coating, or a biologically active coating.

17. A method of performing a surgical procedure comprising the steps of:
introducing a catheter through a patient's vasculature until the catheter is positioned adjacent a target site;
deploying a vascular device from a delivery sheath connected to a first end portion of the catheter such that the vascular device is positioned in a desired orientation within the patient's vasculature;
removing the catheter from the patient's vasculature;
reversing the catheter such that a retrieval sheath connected to a second end portion of the catheter opposite the first end portion is oriented for insertion into the patient's vasculature;
re-introducing the catheter into the patient's vasculature such that the retrieval sheath is positioned adjacent the vascular device;
drawing the vascular device into the retrieval sheath; and
removing the catheter and the vascular device from the patient's vasculature; wherein the delivery sheath is fixed to the first end portions of the catheter, and the retrieval sheath is fixed to the second end portion of the catheter.

18. The method of claim 17 further comprising the step of positioning a guidewire within the patient's vasculature.

19. The method of claim 18 further comprising the step of back-loading the guidewire into the delivery sheath.

20. The method of claim 19, wherein the step of introducing the catheter includes advancing the catheter over the guidewire.

21. A catheter comprising:
an elongated member defining a longitudinal axis, and having opposite first and second end portions;
a delivery sheath connected to the first end portion of the elongated member, the delivery sheath including a first internal cavity configured to receive a vascular device;
a retrieval sheath connected to the second end portion of the elongated member, the retrieval sheath including a second internal cavity configured to receive the vascular device, the delivery sheath and the retrieval sheath being connected to the elongated member such that the catheter is formed as a single, unitary structure, wherein the retrieval sheath includes a rolled tip extending inwardly toward a central longitudinal axis defined by the elongated member; wherein the delivery sheath is fixed to the first end portions of the elongated member, and the retrieval sheath is fixed to the second end portion of the elongate member.

22. The catheter of claim 21, wherein the elongated member comprises a first material, the first material being of sufficiently rigidity and flexibility to facilitate advancement of the catheter through a patient's vasculature.

23. The catheter of claim 22, wherein the delivery sheath comprises a second material different than the first material.

24. The catheter of claim 23, wherein the retrieval sheath comprises the second material.

25. The catheter of claim 24, wherein the second material is more pliable than the first material.

26. The catheter of claim 22, wherein the delivery sheath and the retrieval sheath each include at least one radiopaque portion.

27. The catheter of claim 22, further including a hydrophobic coating, a hydrophilic coating, or a biologically active coating.

28. The catheter of claim 22, wherein the delivery sheath includes a first sidewall port configured to receive a wire.

29. The catheter of claim 28, wherein the delivery sheath further includes a second sidewall port configured to receive the wire, the second sidewall port being spaced longitudinally from the first sidewall port.

30. A catheter comprising:
an elongated member defining a longitudinal axis, and having opposite first and second end portions, and an outer wall defining a lumen extending through the elongated member;
a delivery sheath connected to the first end portion of the elongated member, the delivery sheath including a first internal cavity configured to receive a vascular device, wherein the first internal cavity is in communication with the lumen extending through the elongated member; and
a retrieval sheath connected to the second end portion of the elongated member, the retrieval sheath including a second internal cavity configured to receive the vascular device, the delivery sheath and the retrieval sheath being connected to the elongated member such that the catheter is formed as a single, unitary structure; wherein the delivery sheath is fixed to the first end portions of the catheter, and the retrieval sheath is fixed to the second end portion of the catheter.

31. The catheter of claim 30, wherein the first internal cavity of the delivery sheath defines an internal transverse cross-sectional dimension greater than an internal transverse cross-sectional dimension defined by the lumen extending through the elongated member.

32. The catheter of claim 31, wherein the second internal cavity of the retrieval sheath defines an internal transverse cross-sectional dimension larger than the internal transverse cross-sectional dimension defined by the lumen extending through the elongated member.

* * * * *